(12) United States Patent
Semenkovich

(10) Patent No.: US 6,528,637 B1
(45) Date of Patent: Mar. 4, 2003

(54) FATTY ACID SYNTHASE MRNA BINDING PROTEIN

(75) Inventor: Clay F. Semenkovich, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/551,268

(22) Filed: Apr. 18, 2000

Related U.S. Application Data

(62) Division of application No. 09/223,264, filed on Dec. 30, 1998.
(60) Provisional application No. 60/071,043, filed on Jan. 13, 1998.

(51) Int. Cl.[7] .......................... C07H 21/02; C12N 15/11
(52) U.S. Cl. .................... 536/24.1; 536/23.2; 536/23.5; 536/23.1; 435/183; 435/193; 435/6; 435/15; 429/94.1; 429/94.2; 429/94.5
(58) Field of Search ............................... 536/23.1, 23.2, 536/23.5, 24.1; 435/6, 183, 15, 193; 424/94.5, 94.1, 94.2

(56) References Cited

U.S. PATENT DOCUMENTS 5,665,874 A 9/1997 Kuhajda et al. ............ 536/24.3

OTHER PUBLICATIONS

Dudek and Semenkovich, J. Biol. Chem. vol. 270, pp. 29323–29329 (1995).
Semenkovich et al., J. Lipid Res. vol. 36, pp. 1507–1521 (1995).
Semenkovich et al., J. Biol. Chem. vol. 268, pp. 6961–6970 (1993).
Seip et al., Am. J. Physiol., vol. 268, pp. E229–E236 (1995).
Semenkovich and Heinecke, Diabetes, vol. 45, pp. 327–334 (1997).
Chua et al., Circulation, vol. 94, No. 8, (1996) Abstr. I–397.
Jenner et al., EMBL/GenBank/Database Accession No.: U29344 Aug. 10, (1995) Sequence submitted by Gary Pasternack.
Semenkovich et al., J. Lipid Res., vol. 36, No. 7, (1995) pp 1507–1521.
Epstein et al., Urology, vol. 45, No. 1, (1995) pp. 81–86.
Alo et al., Cancer, vol. 77, No. 3, (1996) pp. 474–482.
Semenkovich, Prog. Lipid Res., vol. 36, No. 1, (1997) pp. 43–53.
Ross, Trends Genetic Res., vol. 12, No. 5, (May 1, 1996) pp. 171–175.
Hentze, TIBS, vol. 19, (Mar. 1994) pp. 101–103.
Li, et al., Amer. J. Physiol., vol. 274, No. 4, (Apr. 4, 1998) pp. e577–e585.

*Primary Examiner*—Rebecca E. Prouty
*Assistant Examiner*—Richard Hutson
(74) *Attorney, Agent, or Firm*—Scott J. Meyer

(57) ABSTRACT

Disclosed is a 178 kDa glucose-inducible human fatty acid synthase (FAS) mRNA binding protein which has been purified to homogeneity and its binding element characterized. This large phosphoprotein binds to a novel repetitive element in the 3' untranslated region (UTR) of the FAS mRNA. In particular, the binding has been mapped to a 37 nucleotide stretch within the first 65 bases of the 3' UTR of mRNA. The binding protein is useful for mediating FAS expression, for regulating lipoprotein secretion and cell growth and for screening of test compounds for activity as inhibitors of FAS.

2 Claims, 8 Drawing Sheets

FATTY ACID SYNTHASE MRNA BINDING PROTEIN

This is a division of application Ser. No. 09/223,264, filed Dec. 30, 1998, which claims the benefit of provisional application Ser. No. 60/071,043, filed Jan. 13, 1998.

FIELD OF THE INVENTION

The present invention relates to glucose regulation of fatty acid synthesis and, more particularly, to a glucose-inducible human fatty acid synthase mRNA binding protein.

Long chain fatty acids are necessary for normal cellular structure and function. De novo synthesis represents an important source of these fatty acids. Critical to this process is the enzyme fatty acid synthase (FAS), a multifunctional protein which synthesizes saturated fatty acids (mostly palmitate) from acetyl-CoA, malonyl-CoA, and NADPH. FAS is believed to be involved in the pathogenesis of such diverse disorders as atherosclerosis and malignancies. FAS overexpression is associated with hyper-triglyceridemia, a common disorder predisposing to atherosclerosis. High levels of FAS predict a poor prognosis in humans with breast cancer.

(NOTE: Literature references on the following background information and on conventional test methods and laboratory procedures well-known to the ordinary person skilled in the art, and other such state-of-the-art techniques as used herein, are indicated by reference numerals in parentheses, and appended at the end of the specification).

BACKGROUND OF THE INVENTION

Chronically elevated concentrations of glucose like those seen in humans with diabetes mellitus are probably toxic. Insulin is important for glucose transport in certain tissues, but the majority of glucose uptake is independent of insulin and proportional to circulating glucose concentrations (6). In insulin-resistant states such as Type II diabetes, the total flux of glucose across certain tissues such as the liver is substantially increased. Glucose alone, independent of hormonal derangements, likely contributes to complications of diabetes such as hyperlipidemia (33).

Exactly how glucose promotes hyperlipidemia is unknown. The liver is central to this process and carbohydrates increase the expression of several hepatic genes involved in intermediary metabolism and lipogenesis including fatty acid synthase, L-type pyruvate kinase, acetyl-CoA carboxylase, ATP-citrate lyase, and malic enzyme (10). This effect is primarily transcriptional but glucose also stabilizes mRNAs for many feeding-responsive hepatic genes (32). Glucose promotes the stability of the message for the insulin receptor (12), another protein central to fuel flow and lipid metabolism.

Regulation of mRNA stability is an important mechanism for altering mammalian gene expression. Messenger RNA half-life depends on at least three components:

1) The enzymes which degrade mRNA;
2) Cis determinants located anywhere in the mRNA but usually in the 3' terminus of the message; and
3) Trans-acting factors which interact with the message to promote or prevent decay.

There are probably a small number of eukaryotic ribonucleases (20). It is likely that regulated message stability depends on the interaction of binding proteins with specific RNA sequences to either promote or prevent access to ribonucleases.

Fatty acid synthase (FAS) is the cytosolic enzyme that synthesizes palmitate from acetyl-CoA, malonyl-CoA, and NADPH (36). It is rate-limiting in the long-term control of fatty acid synthesis (35) and regulated by several different classes of nutrients (8). FAS overexpression occurs in animal models of obesity (16). Carbohydrates stimulate FAS expression and produce hypertriglyceridemia in animals and humans (35,15).

FAS is also relevant to malignancy. Cultured carcinoma cells maintain high levels of endogenous fatty acid synthesis even in the presence of high concentrations of exogenous fatty acids (24). FAS overexpression in breast and prostate carcinomas is a powerful predictor of a poor clinical outcome (1,9). The enzyme is overexpressed in colorectal tumors (27). Glucose transport and catabolism are enhanced in cancer cells (28) suggesting that coordinate regulation of glucose and lipid metabolism characterize the malignant state.

Glucose alone, independent of hormones, stabilizes the FAS message in HepG2 cells (32). In this model system, glucose maintains message levels for several hours while decay is rapid following glucose deprivation (31).

BRIEF DESCRIPTION OF THE INVENTION

In accordance with the invention, it has been found that glucose induces the binding of a novel 178 kDa protein to the fatty acid synthase (FAS) message. This glucose-inducible human FAS mRNA binding protein has been purified to homogeneity and its binding element defined. This large phosphoprotein binds to a novel repetitive element in the 3' untranslated region (UTR) of the FAS mRNA. In particular, the binding has been mapped to a 37 nucleotide stretch within the first 65 bases of the 3' UTR of mRNA.

Purification and characterization of the novel 178 kDa protein of the invention herein was carried out in conjunction with a determination of the underlying mechanisms whereby glucose stabilizes the mRNA for FAS and its relationship to diverse human disorders, including hyperlipidemia, obesity and malignancy.

More specifically, as described hereinbelow in greater detail:

RNA gel mobility shift assays were used to demonstrate that human HepG2 cells and bovine liver contain a cytoplasmic factor which binds specifically to the 3' terminus of the human FAS mRNA.

D-glucose increased RNA binding activity by 2.02-fold ($p=0.0033$) with activity peaking three hours after glucose feeding.

Boiling or treatment of extracts with proteinase K abolished binding.

UV crosslinking of the FAS mRNA-binding factor followed by SDS-PAGE resolved a proteinase K-sensitive band with an apparent molecular mass of 178±7kD.

The protein was purified to homogeneity using nondenaturing polyacrylamide gels as an affinity matrix.

Acid phosphatase treatment of the protein prevented binding to the FAS mRNA, but binding activity was unaffected by modification of sulfhydryl groups and was not $Mg^{++}$-or $Ca^{++}$-dependent.

Deletion and RNase T1 mapping localized the binding site of the protein to 37 nucleotides characterized by the repetitive motif ACCCC and found within the first 65 bases of the 3' UTR.

Hybridization of the FAS transcript with an oligonucleotide antisense to this sequence abolished binding.

These findings indicate that a 178 kD glucose-inducible phosphoprotein binds to an $(ACCCC)_n$-containing sequence in the 3' UTR of the FAS mRNA within the same time frame that glucose stabilizes the FAS message. This protein is thus believed to participate in the post-transcriptional control of FAS gene expression.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in conjunction with the accompanying drawings.

A radiolabeled transcript containing the distal coding region and the first 400 bases of the 3' UTR for the FAS mRNA (transcript 3 of FIG. 6) was generated by in vitro transcription.

For each lane, 10 μg of HepG2 S100 cytosolic extract was incubated with radiolabeled sense FAS RNA followed by treatment with RNase T1 and electrophoresis in non-denaturing gels.

Incubations were performed in the presence (lanes 3–5 and 7–12) and absence (lanes 1,2,6) of nonradioactive competitor RNA.

The position of the gel-shifted band is indicated by arrowheads. The position of free, RNase T1-digested probe is indicated at the bottom of the gel.

Lane 1 contained probe only (P) without extract.

Lanes 3–5 represent incubations performed in the presence of a 1–10 fold molar excess of nonradioactive FAS sense RNA.

Lanes 7–9 represent incubations performed in the presence of a 1–10 fold molar excess of nonradioactive FAS antisense RNA.

Lanes 10–12 represent incubations performed in the presence of a 1–10 fold molar excess of nonradioactive lipoprotein lipase sense RNA.

FIG. 2, in three parts, A, B, and C, shows that binding of the FAS mRNA binding factor is induced by D-glucose.

Figure 2A:
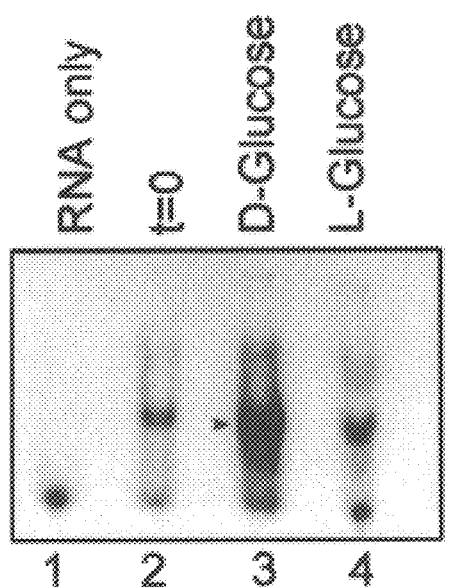

FIG. 2A shows the results of a representative gel mobility shift assay comparing RNA binding activity of equal amounts of HepG2 cytosolic extract (within the linear response range of the assay) at time zero (lane 2), and three hours after feeding 4500 mg/L D-glucose (lane 3) or the same concentration of L-glucose (lane 4).

Figure 2B:
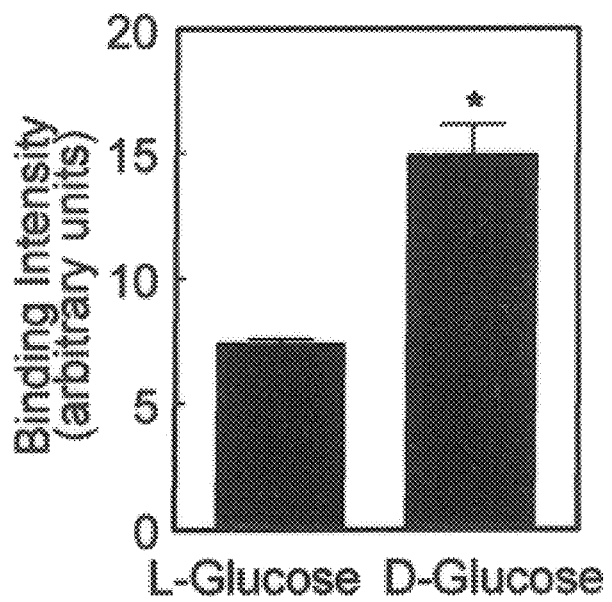

FIG. 2B shows the results of three independent experiments identical to FIG. 2A as quantitated by densitometry. Binding activity (in arbitrary units, mean±sem) of the gel-shifted band was 14.95±1.20 for D-glucose and 7.40±0.18 for L-glucose (p=0.0033).

Figure 2C:
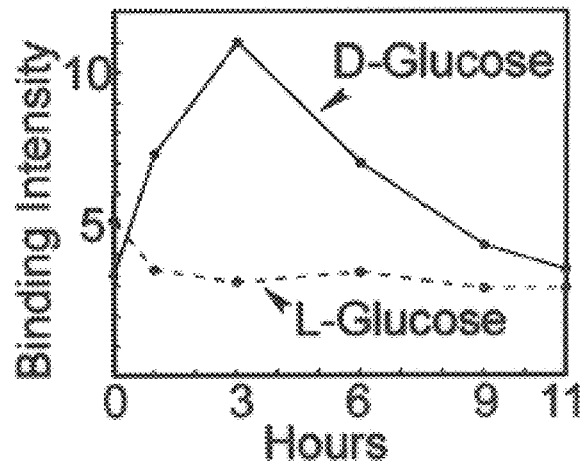

FIG. 2C shows the results of a representative time course experiment. Extracts were prepared at various times following treatment with 4500 mg/ml D- or L-glucose, subjected to gel shift assays, and results were quantitated by densitometry.

FIG. 3, in two parts, A and B, shows that the FAS mRNA binding factor is a protein.

Figure 3A:
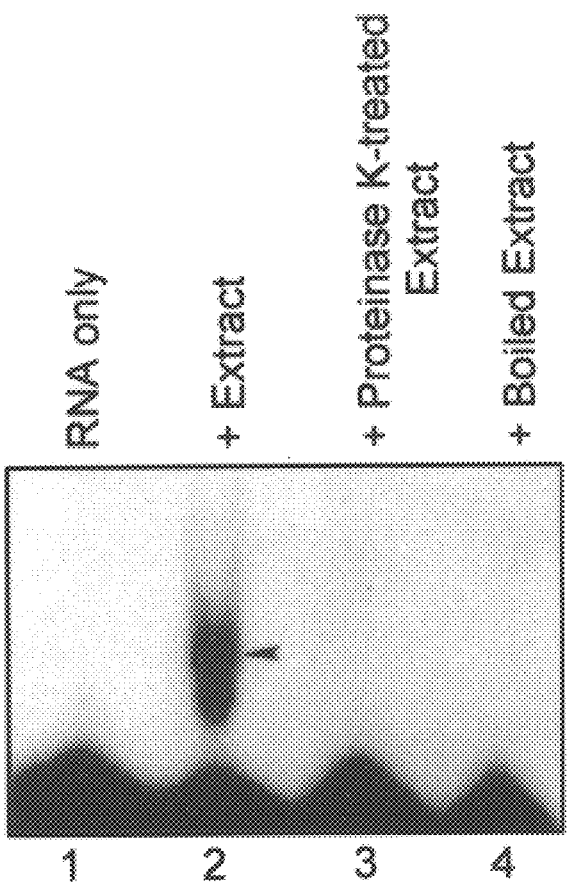

For FIG. 3A, lanes contained radiolabeled FAS RNA in the absence (lane 1) or presence (lanes 2–4) of 20 μg of HepG2 cytosolic protein.

HepG2 extracts were subjected to no treatment (lane 2), incubation with 500 μg/ml proteinase K at 37° C. for one hour (lane 3), or heating at 100° C. for 5 min. (lane 4) prior to t he addition of FAS RNA.

Another band of faster mobility is seen just below the dominant band indicated by the arrowhead in lane 2. This lower band likely represents a proteolytic fragment of the upper band as described in the text.

Free, RNase T1-digested probe appears in each lane along the bottom of the gel.

Figure 3B:
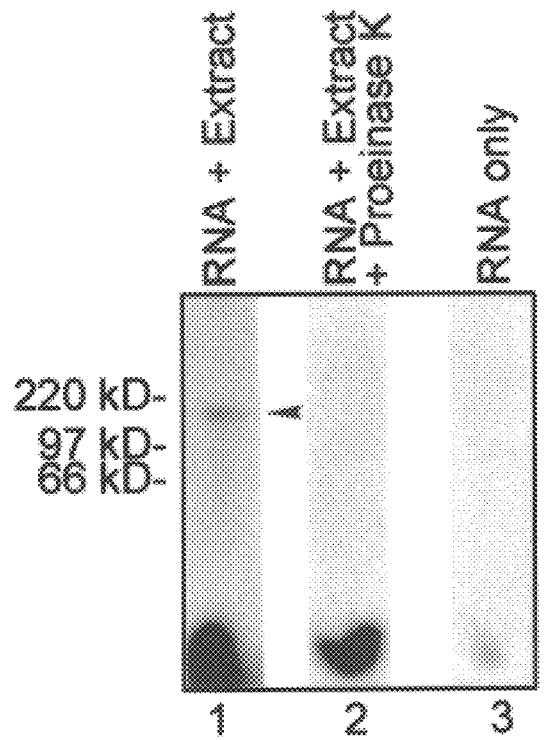

For FIG. 3B, gel mobility shift assays were performed using multiple lanes of native gels. Gels were UV crosslinked, then bands denoted by the arrowhead in FIG. 3A were cut out and either directly subjected to SDS-PAGE in a 6% gel (lane 1) or treated with 500 μg/ml proteinase K at 37° C. for one hour before electrophoresis (lane 2). Appropriate regions of native gels loaded with lysis buffer instead of HepG2 extracts were also cut out and electrophoresed (lane 3). The arrowhead shows the 178 kD position.

Figure 4:
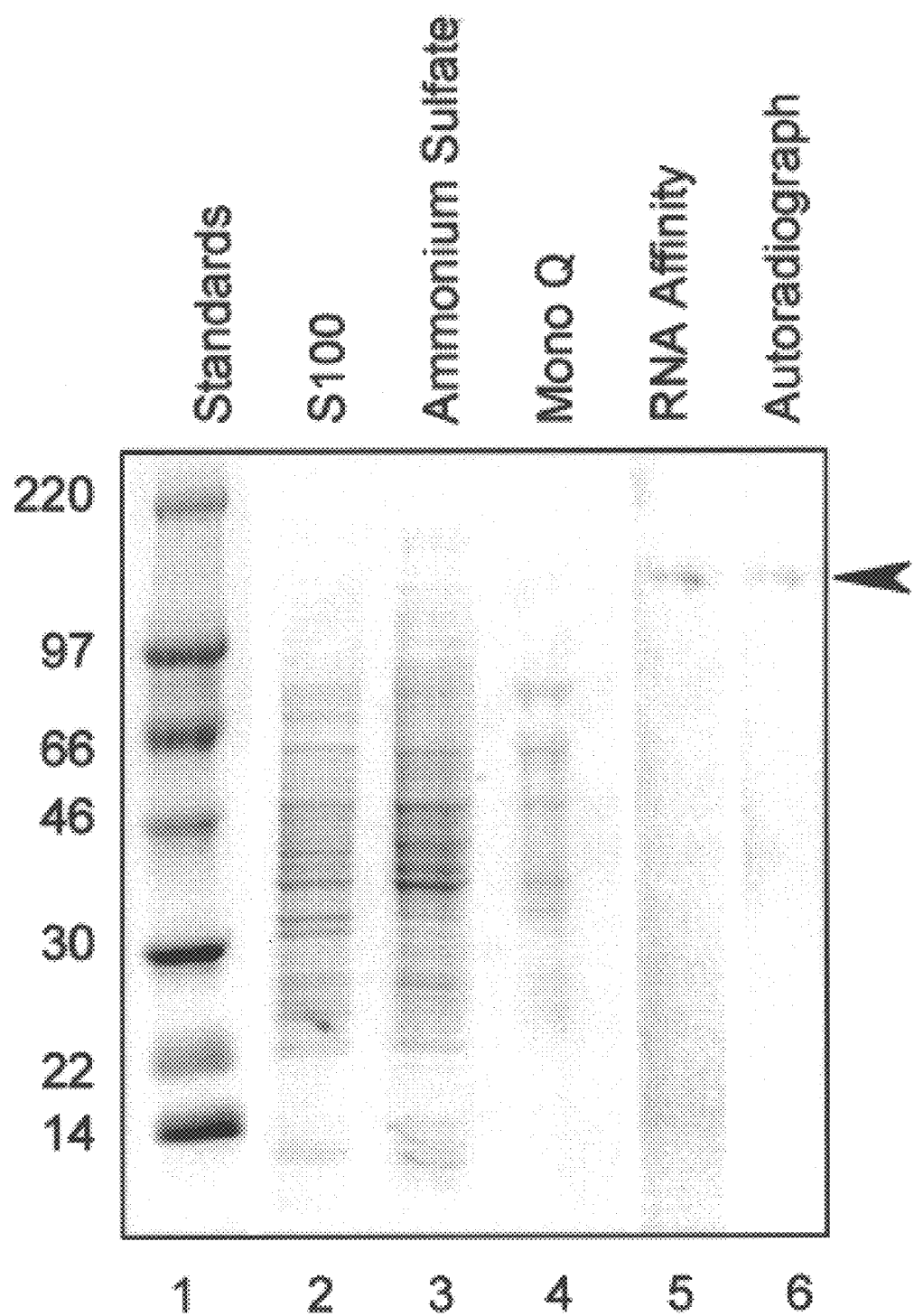

FIG. 4 shows the purification of the 178 kD FAS mRNA binding protein. HepG2 extracts were processed as described in Methods hereinbelow.

Protein yields at each step of the purification are shown in Table 1, hereinbelow.

Lanes 2–4 were loaded with 20 μg of protein per lane.

Lane 5 represents 10 μg of purified protein as determined by comparison with standards.

Lanes 1–5 represent amido black B staining of a 2–15% gradient gel.

Lane 6 is an autoradiograph of the same gel depicted in lane 5. The 178 kD position is indicated by the arrowhead.

Figure 5:
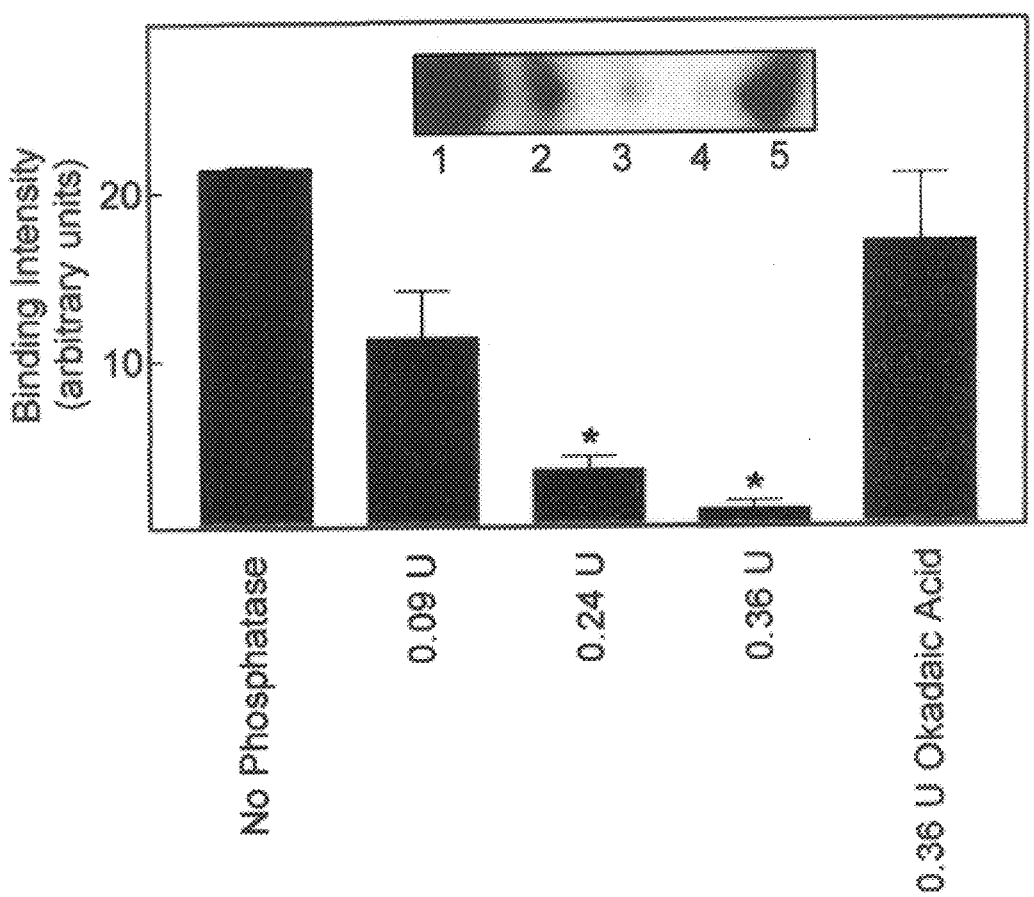

FIG. 5 shows that the FAS mRNA binding protein is a phosphoprotein.

Partially purified protein was incubated in the absence (No Phosphatase) or presence of increasing concentrations of potato acid phosphatase followed by gel shift assay and quantitation by densitometry.

The experiment included a tube containing the highest concentration of potato acid phosphatase (0.36 units) in the presence of 10 μM okadaic acid.

Asterisks indicate that binding activity in the presence of both 0.24 units (p<0.01) and 0.36 units (p<0.001) of phosphatase was significantly different from activity in the absence of phosphatase.

Results represent the mean±sem of three independent experiments.

The inset shows the results of a representative experiment:
lane 1=No phosphatase,
lane 2=0.09 units,
lane 3=0.24 units,
lane 4=0.36 units,
lane 5=0.36 units+okadaic acid.

Figure 6:
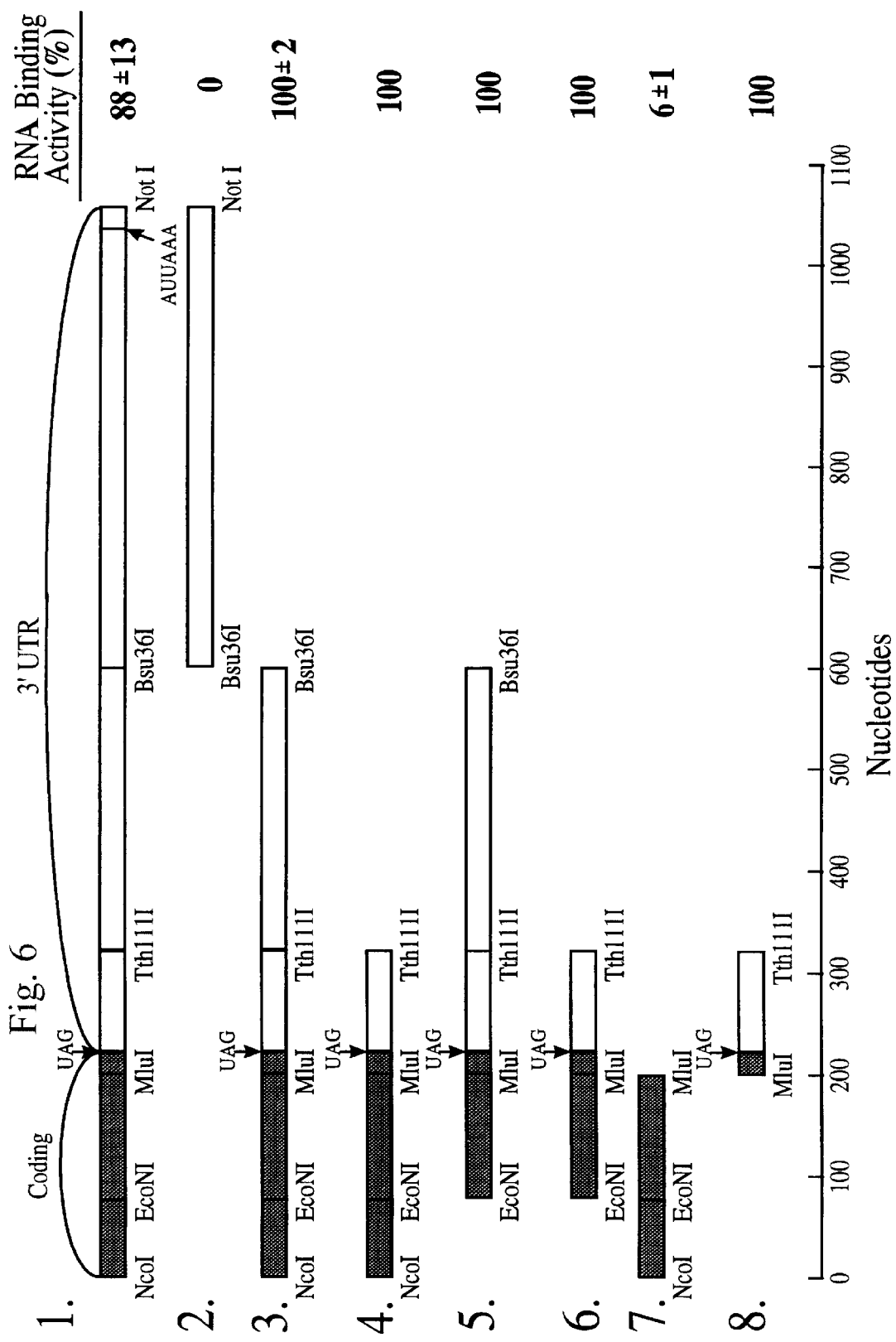

FIG. 6 shows transcripts used to localize the binding element for the 178 kD protein.

Results of gel shift assays for the 178 kD protein are shown on the right (RNA binding Activity in %).

Binding activity was quantitated by densitometry and normalized to the signal for transcript 3.

Each transcript was assayed at least 3 times.

The signals generated by transcripts 1 and 3 were not significantly different (p=0.2976, n=4).

The difference between transcripts 3 and 7 was significant (p<0.0001, n=3).

The positions of the stop codon (UAG) and polyadenylation signal (AUUAAA) are indicated.

Transcript 2 had no RNA binding activity. Transcripts antisense to transcripts 1,3,4, and 5 as well as a sense lipoprotein lipase transcript also had no RNA binding activity.

FIG. 7, in two parts, A and B, shows the identification of the binding element for the 178 kD protein by RNase T1 mapping and oligonucleotide competition.

Figure 7A:
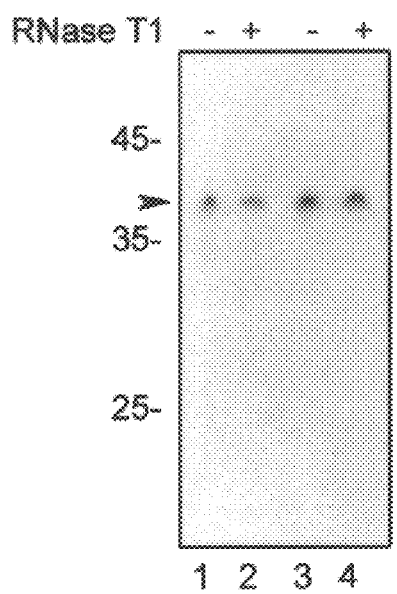

For FIG. 7A, gel shift assays were performed with transcripts 4 and 5 from FIG. 6. RNA protein complexes were excised, eluted, extracted with phenol/chloroform, and precipitated.

RNA was incubated in the presence (lanes 2 and 4) or absence (lanes 1 and 3) of RNase T1, then separated on 15% denaturing polyacrylamide gels and autoradiographed.

Lanes 1–2 show results using transcript 4, and lanes 3–4 show results using transcript 5 from FIG. 6.

Identical results were also obtained using transcript 3 from FIG. 6.

Nucleotide size markers are shown to the left of the FIG. 7A panel and the position of the 37 nucleotide protected fragment is indicated by the arrowhead.

Figure 7B:
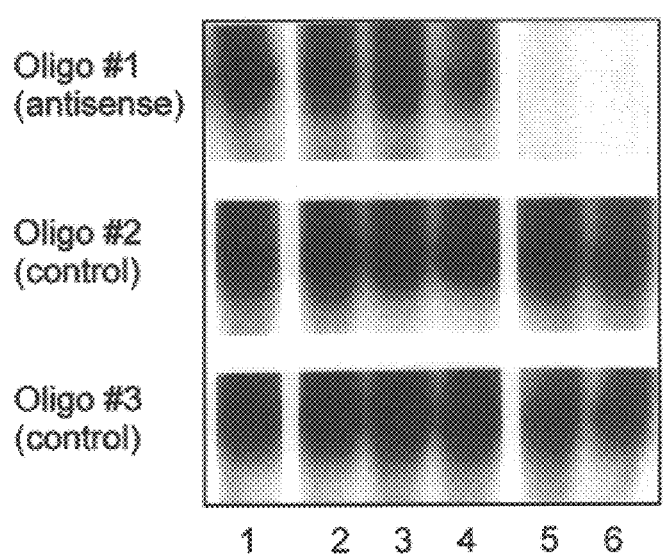

For FIG. 7B, gel shift assays were performed using HepG2 extracts and transcript 4 from FIG. 6 in the presence of competitor oligonucleotides as described in Methods, hereinbelow.

Oligo #1 [SEQ ID NO:1] was antisense to the 37 nucleotides identified in FIG. 7A.

Oligos #2 [SEQ ID NO:2] and #3 [SEQ ID NO:3] were unrelated control sequences.

Lanes 1–6 show results of gel shift assays in the presence of increasing amounts of oligonucleotides.

Oligos were added in the following amounts:

Lane 1=0 ng

Lane 2=4.5 ng

Lane 3=9 ng

Lane 4=18 ng

Lane 5=180 ng

Lane 6=900 ng.

Figure 8:
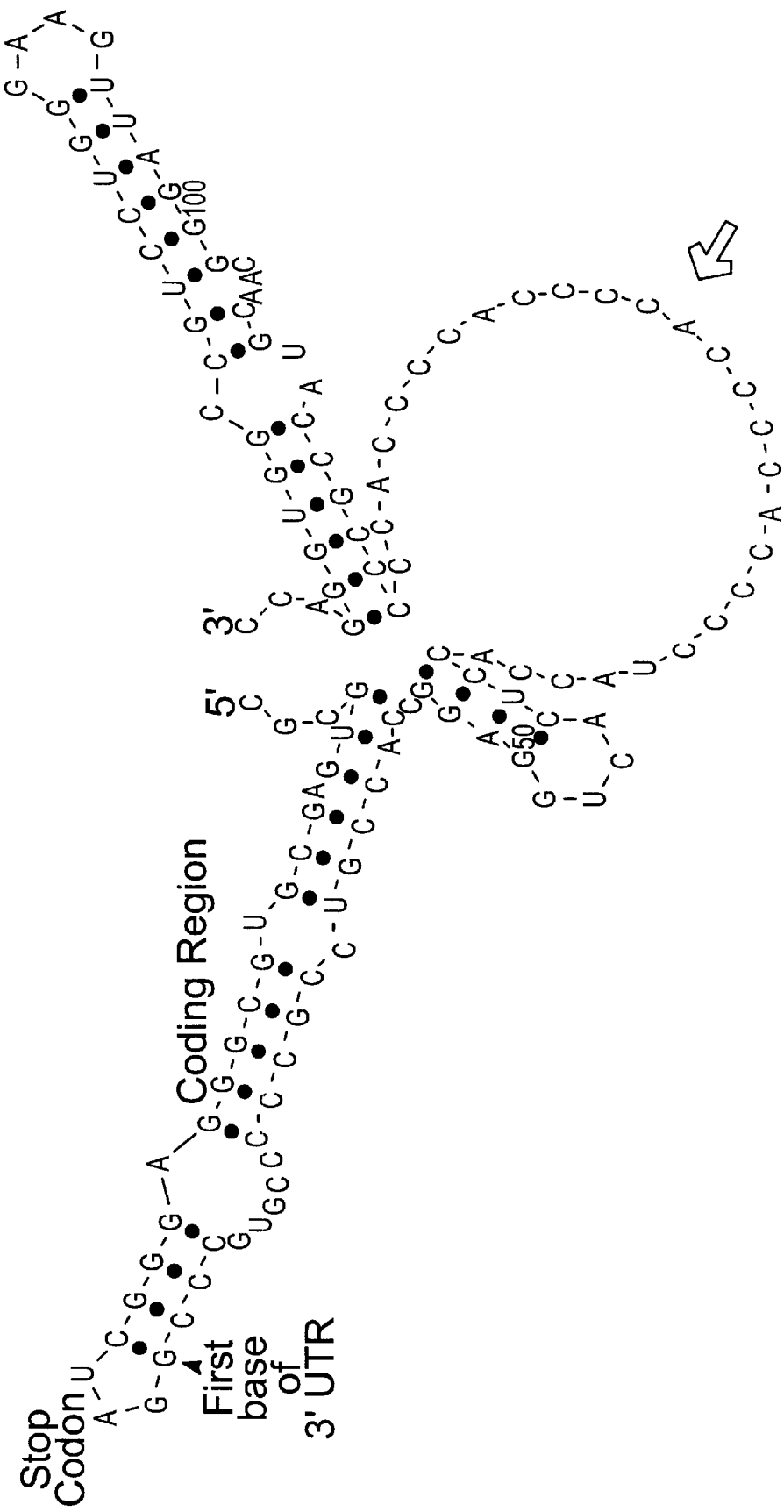

FIG. 8 shows the predicted structure of the 178 kD binding element.

Transcript 8 from FIG. 6 contains 126 nucleotides [SEQ ID NO:7] which were folded using the RNA secondary structure program of Michael Zuker, Washington University School of Medicine, at www.ibc.wustl.edu/~zuker/rna/form1.cgi.

The predicted free energy for this structure is −43.2 kcal/mol.

This program predicts one other potential structure which was not consistent with the RNase T1 mapping data.

The binding element is indicated by the arrow.

Points of RNA hybridization are indicated by solid circles.

The location of the stop codon (UAG) and the first base of the 3' UTR are also indicated.

In order to illustrate the invention in further detail, the following specific laboratory examples were carried out.

Although specific examples are thus illustrated herein, it will be appreciated that the invention is not limited to these specific, illustrative examples or the details therein.

EXAMPLES

METHODS

Tissue Culture Reagents and Culture Conditions. Glucose-free/bicarbonate-free RPMI-1640, bicarbonate, D-glucose, L-glucose, and bovine serum albumin (BSA, fraction V) were purchased from Sigma. Fetal bovine serum (FBS) was purchased from Intergen. MEM was provided by the Washington University Tissue Culture Support Center.

HepG2 cells were grown in MEM+10% FBS for large scale preparation of cell extracts and protein purification. For experiments involving glucose regulation, cells were treated as described (31,32). HepG2 cells are human hepatoma cells widely distributed throughout the world and have been readily available to the public without restriction for many years from the depository of the American Type Culture Collection, Rockville, MD.

On day 3 or 4 after passage, cells were fed MEM+10% FBS. On day 5 or 6, culture medium was replaced with RPMI-1640+10% FBS+4500 mg/L D-glucose. Twenty-four hours later, medium was removed and dishes were washed twice with phosphate-buffered saline (PBS) at 37° C. The cells were then fed RPMI-1640+3% BSA+4500 mg/ml D-glucose.

Six hours later, the medium was removed and dishes were washed twice with PBS at 37° C. Cells were then fed RPMI-1640+3% BS with 4500 mg/L D-glucose or 4500 mg/L L-glucose.

Preparation of S100 Cytosolic Extracts. For HepG2 cells, medium was removed and dishes were washed twice with PBS at 4° C. The cells were scraped in lysis buffer (250 μl/100mm dish) consisting of 10 mM Tris (pH 7.4), 40 mM KC1, 0.15 mM spermine, 2 mM EDTA, 5 mM dithiothreitol, and 100 μg/ml phenylmethylsulfonyl fluoride. Cells were homogenized using a Dounce homogenizer by twenty strokes of a tight-fitting pestle. Nuclei were removed by centrifugation at 13,000 g for ten min. This supernatant was centrifuged at 100,000 g for one hour in a Beckman TL-100 ultracentrifuge to yield a polysome-free extract (S100). Protein concentration was determined using the BCA Protein Assay (Pierce).

Bovine liver was obtained from a local slaughterhouse (Schneider Packing Co., St. Louis). Immediately after sacrifice, livers were placed in a plastic bag and packed in ice. At the lab, livers were perfused with saline to remove blood then homogenized in lysis buffer using a Waring blender. Nuclei were sedimented and then the supernatant was spun at 100,000 g to yield a polysome-free extract.

Preparation of RNAs by In Vitro Transcription. The parent plasmid used as a template for transcription of the FAS full-length 3' untranslated region (UTR) was constructed by subcloning an Nco I-Not I restriction fragment of the human FAS cDNA (from nucleotides 1190 to 2237 as numbered in reference 31) into pGEM-5Z. This fragment (FIG. 6, transcript 1) contained the coding region for the 72 carboxyl-terminal amino acids of the FAS protein and the entire 806 bases of the 3' UTR. Several additional FAS plasmids (see FIG. 6) were derived from this construct by standard cloning techniques. Templates were linearized and gel-purified before in vitro transcription.

Radiolabeled FAS RNA probes were prepared using T7 RNA polymerase (sense) or SP6 (antisense) and $^{32}$P-CTP and purified using NucTrap columns (Stratagene) before use in gel mobility shift assays. Nonradioactive transcripts used for competition studies were prepared in the same way except unlabeled CTP was used for transcription reactions. The plasmid used as a template for transcription of a portion of the coding region of the lipoprotein lipase message has previously been described by Seip et al (30).

All of the RNAs generated by in vitro transcription were treated identically. Probes were frozen at −70° C. immediately following their preparation. The transcripts were thawed gradually at room temperature prior to use in gel mobility shift assays.

Gel Mobility Shift Assays. Binding reactions were performed with S100 cytosolic extract and $0.5-1.0 \times 10^5$ cpm of $^{32}$P-labeled RNA in binding buffer (10 mM Tris [pH 7.4], 2 mM EDTA, 40 mM KCl, and 5 mM dithiothreitol). For competition experiments, competitor transcripts, polyribonucleotides, or oligonucleotides were added before the addition of labeled RNA.

Binding reactions were incubated for 10 min. at 4° C. Five units of RNase T1, which degrades single-stranded RNA not bound to protein, was then added and the incubation was continued for 10 min. at room temperature. The binding reactions were then subjected to electrophoresis through a 6% nondenaturing polyacrylamide gel. Gels were autoradiographed at −70° C. for 4–24 hours.

Ultraviolet Crosslinking of the RNA-Protein Complex. Multiple lanes of 6% non-denaturing gels were loaded with the products of binding reactions, some of which contained radiolabeled RNA only. Following electrophoresis, gels were UV irradiated at 270,000 $\mu$J/cm$^2$.

Gels were autoradiographed, then radiolabeled bands were excised from lanes loaded with extracts; corresponding gel regions were also excised from lanes run with RNA only. Samples were pooled and incubated in an equal volume of Laemmli electrophoresis buffer at 50° C. for 30 min. then at 100° C. for one hour. Eluates from lanes containing extracts were separated into two aliquots, one of which was treated with proteinase K and one of which was not. Samples were subjected to SDS-PAGE in 6% gels then autoradiographed at −70° C.

Size Exclusion Chromatography. S100 cytosolic extracts from either HepG2 cells or bovine liver were precipitated with 25–45% ammonium sulfate. After dialysis against lysis buffer, samples were loaded onto Superose 6 columns equilibrated with 0.9 M NaCl+0.2 mM EDTA+0.2 g/L NaN$_3$. Fractions of 0.5 ml were collected at a flow rate of 0.4 ml/min and assayed for RNA binding activity by gel mobility shift assay.

Ion Exchange Chromatography. Following ammonium sulfate fractionation, samples were applied to prepacked anion (Mono Q) or cation exchange columns (Mono S) using a Pharmacia FPLC.

For the Mono S column, both 50 mM malonate (pH 5.0) and 50 mM MES (pH 6.0) were used for column equilibration in separate experiments. For the Mono Q column, equilibration was performed using 20 mM Tris (pH 7.5); the elution buffer was 20 mM Tris; (pH 7.5)+0–1.0 M KCl.

For both ion exchange columns, the flow rate was 0.5 ml/min and collected fractions were assayed for RNA binding activity. The binding protein did not bind to a Mono S column under a variety of conditions. The protein did bind to a Mono Q column and was eluted with 0.3 M KCl at pH 7.5.

RNA Binding Protein Purification. In a typical purification, S100 cytosolic extracts were prepared from approximately 10$^9$ HepG2 cells. After fractionation with 25–45% ammonium sulfate and dialysis, samples were subjected to anion exchange chromatography as described above.

Fractions containing the RNA binding protein were pooled, concentrated with Centricon-30 fibers at 5000 g, then subjected to a large scale gel shift procedure using 40–45 nondenaturing polyacrylamide gels.

Bands were cut out and placed into an electroelution apparatus (BioRad model 422). Elution was performed at 10 mA/glass tube for 5 hours in 1X TBE. Samples were desalted using Centricon filters then subjected to SDS-PAGE using 2–15% gradient gels. Gels were stained with amido black B followed by autoradiograph at −70%.

Dephosphorylation of the RNA Binding Protein. S100 extracts were subjected to ammonium sulfate fractionation and anion exchange chromatography. Partially purified protein was incubated with potato acid phosphatase (Boehringer Mannheim) in MOPS (pH 6.5), 1 mM MgCl$_2$, 100 mM KCl, 0.2 mM leupeptin for 30 minutes at 30° C. as described by Kwon and Hecht (17). The phosphatase inhibitor okadaic acid (10 $\mu$M) was added to some samples before the incubation.

RNase T1 Mapping. Gel mobility shift assays were performed using the 25–45% ammonium sulfate fraction from HepG2 cells. Bands were cut from the gel and electroeluted as described above.

Samples were extracted with phenol/chloroform then ethanol precipitated. Radioactive RNA (~10,000 cpm) was separated into two aliquots, one of which was digested with 20 units of RNase T1 at room temperature for 30 min. The second aliquot was sham digested. Samples were then separated on a 15% denaturing polyacrylamide gel with end-labeled size markers and autoradiographed.

Oligonucleotide Competition. Radiolabeled RNA was heated to 75° C. for 10 min., a competitor oligonucleotide (oligo #1, #2 or #3) at various concentrations was added, and the mixture was gradually cooled to room temperature over 30–60 min. to allow hybridization of the oligonucleotide with the RNA transcript.

The RNA:DNA hybrid was then incubated with HepG2 extracts and assayed for gel shift activity. The sequences of the competitor oligos were:

Oligo #1-GGGGGTGGGG TGGGGTGGGG TGGG-GATGGT GGAGTGA [SEQ ID NO:1]

Oligo #2-GATCTAGCTT CCCGCTGATG AGTCCGT-GAG GACGAAACAT GCCGGCA [SEQ ID NO:2]

Oligo #3-GATCTGCCGG CATGTTTCGT CCTCACG-GAC TCATCAGCGG GAAGCTA [SEQ ID NO:3]

RESULTS

Figure 1:
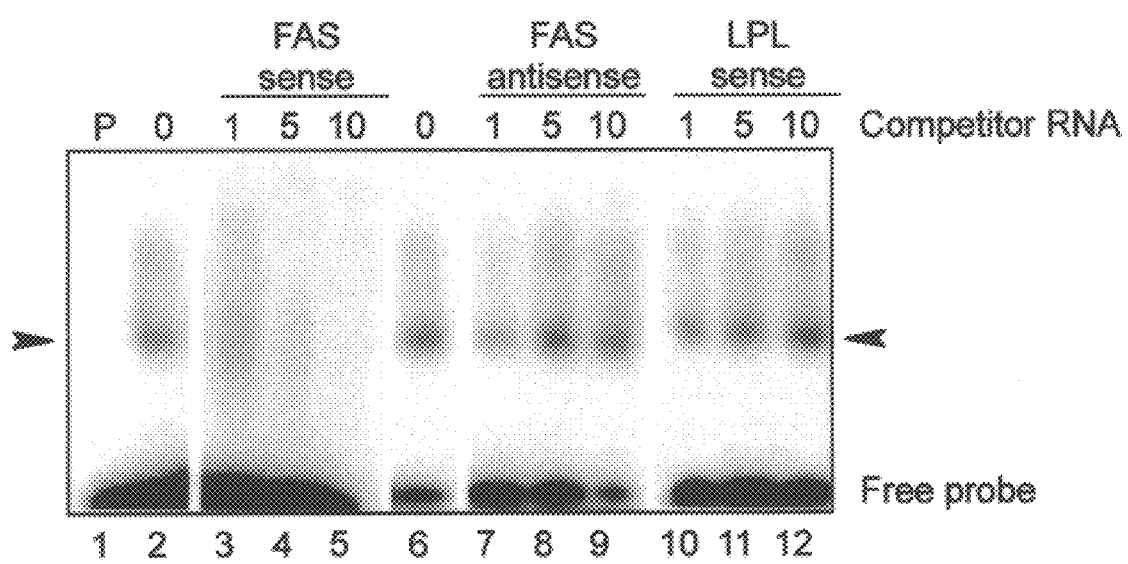
FIG. 1 shows gel mobility shift assays that identify a cytosolic HepG2 factor binding specifically to the 3' terminus of the human FAS mRNA.

When HepG2 extracts were incubated with a transcript corresponding to the FAS 3' terminus, a discrete band was seen in RNA gel shift assays (FIG. 1, lane 2) that did not appear with RNA alone (lane 1).

The addition of a 10-fold molar excess of nonradioactive FAS sense transcript essentially eliminated the gel shift signal (lane 5) while nonradioactive FAS antisense (lane 10) and LPL sense (lane 12) transcripts had no effect. Identical results were seen in five independent experiments.

In other experiments, the addition of up to a 100-fold molar excess of the FAS antisense and LPL sense transcripts had no effect on binding. No complexes were seen when HepG2 extracts were incubated with radiolabeled lipoprotein lipase RNA.

Polyribonucleotides did not compete with $^{32}$P-labeled FAS RNA for binding. In two independent experiments, a 100-fold molar excess of FAS sense transcript eliminated binding but the same molar excess of polyadenylic acid, polyuridylic acid, polyguanidylic acid and polycytidylic acid had no effect.

Binding activity was also present in cytoplasmic extracts from bovine liver. It was originally intended to purify and characterize the protein from bovine liver since it was readily available, but levels of expression were lower in cow liver than HepG2 cells and the latter were easier to manipulate.

The intensity of the gel-shifted band was dependent on the input protein in the assay. In five independent experiments, band intensity increased linearly with protein concentrations from 5 to 20 µg.

Glucose regulates the expression of the FAS mRNA-binding factor (FIG. 2). When cells were cultured in serum-free medium, D-glucose (FIG. 2A, lane 3) but not L-glucose (FIG. 2A, lane 4) increased binding activity in gel shift assays. At the three-hour time point in three independent experiments using protein concentrations within the linear response range of the assay, binding intensity (arbitrary units, mean±sem) as shown in FIG. 2B was 14.95±1.20 with D-glucose and 7.40±0.18 for L-glucose (p=0.0033 by unpaired, two-tailed t test).

The Time course for the glucose-induced increase in binding is shown in the representative experiment of FIG. 2C. After feeding 4500 mg/L D-glucose, binding intensity increased by one hour and peaked at 3 hours. The return to baseline was variable, occurring between 6 hours and 11 hours after feeding. L-glucose had no effect. Results were confirmed in three independent experiments.

Treatment of HepG2 extracts with proteinase K or boiling abolished the binding activity (FIG. 3A). The same results were seen in three independent experiments.

Lane 2 of FIG. 3A shows a dominant upper band (denoted by the arrowhead) as well as a lower band with faster mobility. This lower band probably represents a degradation product. It was faint in fresh extracts and increased in intensity over time.

The band at the arrowhead in FIG. 3A was resolved by SDS-PAGE after UV crosslinking as described in Methods, hereinbefore. Bands were cut from multiple lanes, eluted, pooled, and electrophoresed in SDS gels (FIG. 3B). The FAS mRNA-binding protein (arrowhead, FIG. 3B, lane 1) analyzed under these conditions had an apparent molecular mass of 178±7 kD (mean±sem of four independent experiments).

In two of the four experiments, despite the fact that only the upper, dominant band was cut from native gels, SDS-PAGE showed a lower molecular weight protein just below the 178 kD band consistent with the hypothesis that the pattern sometimes seen in gel shift assays is due to proteolysis. The 178 kD signal did not appear when eluted bands were treated with proteinase K before SDS-PAGE (FIG. 3B, lane 2) and was absent from lanes without extracts (lane 3).

Since the apparent size as determined by SDS-PAGE included crosslinked ribonucleotides, the molecular weight of the FAS RNA binding protein was also determined by gel filtration chromatography as described in Methods, hereinbefore. Using either HepG2 or bovine liver extracts, the fractions with RNA binding activity eluted at an apparent molecular weight of 160–170 kD.

The protein was purified as described in Methods, hereinbefore, from HepG2 S100 extracts by a combination of ammonium sulfate precipitation, anion exchange chromatography and an affinity step. Instead of making an RNA affinity column, nondenaturing polyacrylamide gels were used as the chromatography matrix.

Preparative scale gels were UV crosslinked and autoradiographed, then bands representing the RNA binding protein were excised and electroeluted. Results of a typical purification are shown in FIG. 4. Protein yields at each step of the purification are shown in Table 1. In FIG. 4, lane 6 is an autoradiograph of the purified protein from lane 5. The protein is visible after autoradiography because radiolabeled FAS RNA was UV crosslinked to the protein during purification. The same results were seen in four independent purifications.

Purification of the 178 kD protein allowed defining of its properties. Phosphorylation is required for the activity of some RNA binding proteins (17,19). Acid phosphatase decreased binding activity of Mono Q-purified protein in a dose-dependent fashion, an effect that was reversed with the phosphatase inhibitor okadaic acid (FIG. 5). Results in FIG. 5 represent the mean±sem of three independent experiments.

The iron responsive protein (14), the AU binding factor (19) and a protein which binds to the c-myc message (26) represent examples of RNA binding proteins which require intact sulfhydryl groups for binding activity.

To test the role of sulfhydryl groups in the activity of the human FAS mRNA binding protein, Mono Q-purified protein was treated with the SH-oxidizing agent diamide (0–10 mM) or the SH-alkylating agent NEM (N-ethylmaleimide, 0–2 mM) in the presence or absence of DTT. In three independent experiments, modification of sulfhydryl groups had virtually no effect on RNA binding activity.

Divalent cations are required by some RNA binding proteins (19). In four independent experiments using Mono Q-purified protein, magnesium concentrations between 0 and 4 mM and calcium concentrations between 0 and 2 mM had no effect on gel shift activity.

Another important property of the 178 kD protein is its binding element. A series of deletion plasmids were constructed and used to generate transcripts for gel shift assays (FIG. 6). Binding activity was normalized to the signal for transcript 3 in FIG. 6. The transcript representing the entire 3' terminus of the message (transcript 1) tended to have lower binding activity compared to transcript 3 (88±13 vs 100±2, p=0.2976).

Transcript 2, representing the distal 3' UTR, had no binding activity. Transcripts antisense to transcripts 1,3, 4, and 5 also had no binding activity. Activity for transcript 7 was 6% of the activity of transcript 3(6±1 vs 100±2, p<0.0001). Full binding activity was retained by transcript 8, a 126 nucleotide transcript containing the proximal 3' UTR.

The specific sequence mediating high level binding activity was identified within the first 65 bases of the FAS 3' UTR. RNase T1 mapping using transcripts 4 and 5 from FIG. 6 identified a 37 nucleotide fragment (FIG. 7). The fragment did not contain internal Gs because RNase T1 digestion of RNA isolated from bound protein had no effect on the migration of the isolated RNA (FIG. 7A, lanes 2 and 4). There is one G-free region of exactly 37 nucleotides within the FAS 3' UTR. When an oligonucleotide antisense to this sequence (FIG. 7B, Oligo #1) was hybridized to the FAS transcript, RNA binding activity was abolished. Two different control oligonucleotides had no effect.

The most likely secondary structure of transcript 8 from FIG. 6 is shown in FIG. 8 with the G-free binding element indicated by the arrow. The sequence of this element is:

UC-ACUCC-ACC-AUCCCC-ACCCC-ACCCC-ACCCC-ACCCCC. [SEQ. ID NO:4]

As described above, a large cytosolic protein which binds specifically to a repetitive ACCCC motif in the proximal 3' UTR of the human FAS mRNA has been purified to homogeneity. Binding is induced by glucose and requires phosphorylation. Glucose deprivation leads to the rapid decay of FAS mRNA which is prevented by D-glucose feeding (31). Either glucose deprivation is associated with a factor promoting FAS mRNA decay, or glucose feeding is associated with a factor protecting the message from decay.

In the above examples, D-glucose increases 178 kD binding activity precisely within the time frame that D-glucose protects FAS mRNA from decay suggesting that this protein is a protective trans-acting mRNA-binding protein.

Several presumably protective mRNA-binding proteins are induced in response to nutritional or environmental signals. Iron deprivation induces iron responsive protein binding to the transferrin receptor 3' UTR and protects the message from endonucleolytic attack (14).

Estrogens induce protein binding to the vitellogenin 3' UTR in association with message stabilization (7). Hypoxia stabilizes the tyrosine hydroxylase mRNA and increases protein binding to its 3' UTR (5).

AUREs (repeated copies of the sequence AUUUA) are instability elements; several proteins bind AUREs in association with message stabilization (3,37). Tumor necrosis factor a stabilizes glucose transporter 1 (GLUT1) mRNA and induces protein binding to a GC-rich region of the GLUT1 3' UTR (20).

Exactly how protective RNA-binding proteins work is unknown. Binding may block the action of constitutive endonucleases at a critical site in the message. How cytoplasmic message is compartmentalized is poorly understood but the novel glucose-inducible protein described herein could alter FAS mRNA transport to prevent access to cytoplasmic decay complexes.

In the described system, polyribosomes protect FAS mRNA from decay after glucose deprivation (31) raising the possibility that the 178 kD protein promotes the association of the FAS message with the translational apparatus.

The binding activity described herein is believe to be novel, since there does not appear to be any previously reported mRNA binding proteins of similar size. The 178 kD binding element (ACCCC)$_n$, appears to be unique. It resembles the AURE with cytidines substituted for uridines. Recent data suggest that UUAUUUAUU [SEQ ID NO:5] may be the minimal sequence of the AURE conferring instability (38).

If the present element is analogous, the functional motif may be CCACCCCACC [SEQ ID NO:6]; there are three overlapping copies of this sequence in the 178 kD binding element. Many RNA-binding proteins recognize polypyrimidines, but uridines, not cytidines, are generally preferred (22).

A 35 kD cytoplasmic protein that binds the $\beta_2$-adrenergic receptor mRNA (25), and apobec-1, the cytidine deaminase that binds and edits apoB mRNA (2), are examples of RNA binding proteins completed by poly(U). Polyribonucleotides had no effect on the interaction of the 178 kD protein with the FAS mRNA (see Results, above). Mutagenesis of the (ACCCC)$_n$ motif and determining if this sequence can confer glucose-induced stability to unrelated messages will be critical for further characterizing its function.

More than a dozen classic metabolic enzymes have been shown to bind nucleic acids and dinucleotide binding domains common to these enzymes may be involved (13). The iron responsive protein is also an aconitase, catalyzing the conversion of citrate to isocitrate (11). Glyceraldehyde-3-phosphate dehydrogenase binds tRNA (34) and AUREs (23). Catalase binds and stabilizes its own mRNA (4).

From the above, it is seen how glucose can increase the binding of the 178 kD factor to the FAS mRNA. Phosphorylation is required for optimal binding (FIG. 5). It is believed that glucose metabolism induces phosphorylation of the 178 kD protein to promote binding to the FAS mRNA. It is known that glucose regulation of gene expression through phosphorylation occurs in yeast, whereby glucose initiates a complex phosphorylation cascade. Malate dehydrogenase (21) and the transcriptional activator SIP4 (18) are examples of yeast proteins differentially phosphorylated in response to glucose availability.

Glucose transiently increases binding of a large phosphoprotein to an ACCCC repetitive element in the 3' UTR of the human FAS mRNA within the same time frame that glucose prevents FAS mRNA decay.

Since aberrant glucose and lipid metabolism are commonly associated, additional characterization of this protein could further link glycolysis and lipogenesis in such a way that mechanisms underlying such diverse disorders as diabetic dyslipidemia and malignancy are better understood.

TABLE 1

Purification of the Human FAS mRNA Binding Protein

| Purification Step | Protein (mg) | % Recovery |
|---|---|---|
| S100 post-nuclear cytoplasmic extract | 280 | 100 |
| Ammonium Sulfate Fractionation (25–45%) | 42 | 15 |
| Mono Q column | 4 | 1.4 |
| Electroelution of gel-shifted bands | 0.58 | 0.21 |
| SDS-PAGE | 0.01–0.02 | 0.004–0.007 |

The protein was purified from ~10$^9$ HepG2 cells as described in Methods. Binding activity is not reported; the protein aggregates as it is purified, and extracts stored for variable periods of time are not comparable because the protein undergoes proteolysis. Protein concentration was determined using the BCA Protein Assay (Pierce) except at the final step when values were determined by comparison of protein-stained bands with standards.

Various other examples will be apparent to the person skilled in the art after reading the present disclosure without departing from the spirit and scope of the invention. It is intended that all such other examples be included within the scope of the appended claims.

1. Alo, P. L., P. Visca, A. Marci, A. Mangoni, C. Botti, and U. Di Tondo. Expression of fatty acid synthase (FAS) as a predictor of recurrence in stage I breast carcinoma patients. Cancer 77:474–482, 1996.
2. Anant, S., A. J. MacGinnitie, and N. O. Davidson. Apobec-1, the catalytic subunit of the mammalian apolipoprotein B mRNA editing enzyme, is a novel RNA-binding protein. *J. Biol. Chem.* 270:14762–14767, 1995.
3. Chen, C. -Y., Y. You, and A. -B. Shyu. Two cellular proteins bind specifically to a purine-rich sequence necessary for the destabilization function of a c-fos protein-coding region determinant of mRNA instability. *Mol. Cell. Biol.* 12:5748–5757,1992.
4. Clerch, L. B., J. Iqbal, and D. Massaro. Perinatal rat lung catalase gene expression: influence of corticosteroid and hyperoxia. *Am. J. Physiol.* 260: L428–L433, 1991.
5. Czyzyk-Krzeska, M. F., Z. Dominski, R. Kole, and D. E. Millhom. Hypoxia stimulates binding of a cytoplasmic protein to a pyrimidine-rich sequence in the 3'-untranslated region of rat tyrosine hydroxylase mRNA. *J. Biol. Chem.* 269:9940–9945, 1994.
6. Dinneen, S., J. Gerich, and R. Rizza. Carbohydrate metabolism in non-insulin-dependent diabetes mellitus. *N. Engl. J. Med.* 327:707–713, 1992.
7. Dodson, R. E., and D. J. Shapiro. An estrogen-inducible protein binds specifically to a sequence in the 3' untranslated region of estrogen-stabilized vitellogenin mRNA. *Mol. Cell. Biol.* 14:3130–3138, 1994.
8. Dudek S. M., and C. F. Semenkovich. Essential amino acids regulate fatty acid synthase expression through an uncharged transfer RNA-dependent mechanism. *J. Biol. Chem.* 270:29323–29329, 1995.
9. Epstein, J. I., M. Carmichael, and A. W. Partin. OA-519 (fatty acid synthase) as an independent predictor of pathologic state in adenocarcinoma of the prostate. *Urology* 45:81–86, 1995.
10. Goodridge, A. G. Dietary regulation of gene expression: enzymes involved in carbohydrate and lipid metabolism. *Annu. Rev. Nutr.* 7:157–185, 1987.
11. Gray, N. K., S. Quick, B. Goosen, A. Constable, H. Hirling, L. Kuhn, and M. Hentze. Recombinant iron-regulatory factor functions as an iron-responsive-element-binding-protein, a translational repressor and an aconitase. *Eur. J. Biochem.* 218:657–667, 1993.
12. Hauguel-de-Mouzon, S., C. Mrejen, F. Alengrin, F., and E. Van Obberghen. Glucose-induced stimulation of human insulin-receptor mRNA and tyrosine kinase activity in cultured cells. *Biochem. J.* 305:119–124, 1995.
13. Hentze, M. W. Enzymes as RNA-binding proteins: a role for (di)nucleotide-binding domains?*Trends Biochem. Sci.* 19:101–103, 1994.
14. Hentze, M. W., T. Rouault, J. B. Harford, and R. D. Klausner. Oxidation-reduction and the molecular mechanism of a regulatory RNA-protein interaction. *Science* 244:357–359, 1989.
15. Hudgins L. C., M. Hellerstein, C. Seidman, R. Neese, J. Diakun, and J. Hirsch. Human fatty acid synthesis is stimulated by a eucaloric low fat, high carbohydrate diet. *J. Clin. Invest.* 97:2081–2091, 1996.
16. Jones, B. H., J. H. Kim, M. B. Zemel, R. P. Woychik, E. J. Michaud, W. O. Wilkison, and N. Moustaid. Upregulation of adipocyte metabolism by agouti protein: possible paracrine actions in yellow mouse obesity.*Am. J. Physiol.* 270: E192–E196, 1996.
17. Kwon, Y. K., and N. B. Hecht. Binding of a phosphoprotein to the 3' untranslated region of the mouse protamine 2 mRNA temporally represses its translation. *Mol. Cell. Biol.* 13:6547–6557, 1993.
18. Lesage, P., X. Yang, and M. Carlson. Yeast SNF1 protein kinase interacts with SIP4, a $C_6$ zinc cluster transcriptional activator: a new role for SNF1 in the glucose response. *Mol. Cell. Biol.* 16:1921–1928, 1996.
19. Malter, J. S., and Y. Hong. A redox switch and phosphorylation are involved in the post-translational up-regulation of the adenosine-uridine binding factor by phorbol ester and ionophore. *J. Biol. Chem.* 266:3167–3171, 1991.
20. McGowan, K. M., S. Police, J. B. Winslow, and P. H. Pekala. Tumor necrosis factor-α regulation of glucose transporter (GLUT1) mRNA turnover. *J. Biol. Chem.* 272:1331–1337, 1997.
21. Minard, K. I., and L. McAlister-Henn. Glucose-induced phosphorylation of the MDH2 isozyme of malate dehydrogenase in *Saccharomyces cerevisiae*. *Arch. Biochem. Biophys.* 315:302–309, 1994.
22. Morris, D. R., T. Kakegawa, R. L Kaspar, and M. W. White. Polypyrimidine tracts and their binding proteins: regulatory sites for posttranscriptional modulation of gene expression. *Biochemistry* 32:2931–2937, 1993.
23. Nagy, E., and W. F. Rigby. Glyceraldehyde-3-phosphate dehydrogenase selectively binds AU-rich RNA in the AND(+)-binding region (Rossman fold). *J. Biol. Chem.* 270:2755–2763,1995.
24. Pizer, E. S., F. D. Wood, G. R. Pasterack, and F. P Kuhajda. Fatty acid synthase (FAS): a target for cytotoxic antimetabolites in HL60 promyelocytic leukemia cells. *Cancer Res.* 56: 745–751, 1996
25. Port, J. D., L. -Y. Huang, and C. C. Malbon. β-adrenergic agonists that down-regulate receptor mRNA up-regulate a $M_r$35,000 protein(s) that selectively binds to β-adrenergic receptor mRNAs.*J. Biol. Chem.* 267:24103–24108, 1992.
26. Prokipcak, R. D., D. J. Herrick, and J. Ross. Purification and properties of a protein that binds to the C-terminal coding region of human c-myc mRNA. *J. Biol. Chem.* 269:9261–9269, 1994.
27. Rashid, A., E. S. Pizer, M. Moga, L. Z. Milgraum, M. Zahurak, G. R. Pastemak, F. P. Kuhajda, and S. R. Hamilton. Elevated expression of fatty acid synthase and fatty acid synthetic activity in colorectal neoplasia.*Am. J. Path.* 150:201–208, 1997.
28. Rempel,A., S. P. Methupala, and P. L. Pederson. Glucose catabolism in cancer cells: regulation of the Type II hexokinase promoter by glucose and cyclic AMP. *FEBS Lett.* 385:233–237, 1996.
29. Ross, J. Control of messenger RNA stability in higher eukaryotes. *Trends Genetics* 12:171–175, 1996
30. Seip R. L., T. J. Angelopoulos, and C. F. Semenkovich. Exercise induces human lipoprotein lipase gene expression in skeletal muscle but not adipose tissue. *Am. J. Physiol.* 268: E229–E236, 1995.
31. Semenkovich C. F., T. Coleman, and F. T. Fiedorek Jr. Human fatty acid synthase mRNA: tissue distribution, genetic mapping, and kinetics of decay after glucose deprivation. *J. Lipid Res.* 36:1507–1521, 1995.
32. Semenkovich C. F., T. Coleman, and R. Goforth. Physiologic concentrations of glucose regulate fatty acid synthase activity in HepG2 cells by mediating fatty acid synthase mRNA stability. *J. Biol. Chem.* 268:6961–6970, 1993.
33. Semenkovich C. F., and J. W. Heinecke. The mystery of diabetes and atherosclerosis: time for a new plot. *Diabetes* 46:327–334, 1997.
34. Singh, R., and M. R. Green. Sequence-specific binding of transfer RNA by glyceraldehyde-3-phosphate dehydrogenase. *Science* 259:365–368, 1993.
35. Volpe, J. J., and P. R. Vagelos. Mechanisms and regulation of biosynthesis of saturated fatty acids. *Physiol. Rev.* 56:339–417, 1976.
36. Wakil, S. J., J. K. Stoops, and V. C. Joshi. Fatty acid synthesis and its regulation. *Annu. Rev. Biochem.* 52:537–579, 1983.
37. Zhang, W., B. J. Wagner, K. Ehrenman, A. W. Schaefer, C. T. DeMaria, D. Crater, K. DeHaven, L. Long, and G. Brewer. Purification, characterization, and cDNA cloning of an AU-rich element RNA-binding protein, AUF1. *Mol. Cell Biol.* 13:7652–7665, 1993.
38. Zubiaga, A. M., J. G. Belasco, and M. E. Greenberg. The nonamer UUAUUUAUU is the key AU-rich sequence motif that mediates mRNA degradation. *Mol. Cell. Biol.* 15:2219–2230, 1995.

What is claimed is:

1. An isolated and purified binding element of a glucose-inducible, phosphorylated mRNA binding protein which binds to the proximal 3' untranslated region of the human fatty acid synthase mRNA, wherein said binding element consists of the 37 nucleotide sequence of SEQ ID NO:4.

2. A 126 nucleotide transcript containing the proximal 3' untranslated region of the human fatty acid synthase mRNA including the binding element of claim 1 wherein said nucleotide transcript consists of SEQ ID NO:7.

* * * * *

SEQUENCE LISTING

<160> NUMBER OF SEQ ID NOS: 7

<210> SEQ ID NO 1
<211> LENGTH: 37
<212> TYPE: DNA
<213> ORGANISM: Artificial Sequence
<220> FEATURE:
<223> OTHER INFORMATION: /note="synthetic construct"

<400> SEQUENCE: 1
gggggtgggg tggggtgggg tggggatggt ggagtga                    37

<210> SEQ ID NO 2
<211> LENGTH: 47
<212> TYPE: DNA
<213> ORGANISM: Artificial Sequence
<220> FEATURE:
<223> OTHER INFORMATION: /note="synthetic construct"

<400> SEQUENCE: 2
gatctagctt cccgctgatg agtccgtgag gacgaaacat gccggca         47

<210> SEQ ID NO 3
<211> LENGTH: 47
<212> TYPE: DNA
<213> ORGANISM: Artificial Sequence
<220> FEATURE:
<223> OTHER INFORMATION: /note="synthetic construct"

<400> SEQUENCE: 3
gatctgccgg catgtttcgt cctcacggac tcatcagcgg gaagcta         47

<210> SEQ ID NO 4
<211> LENGTH: 37
<212> TYPE: RNA
<213> ORGANISM: Artificial Sequence
<220> FEATURE:
<223> OTHER INFORMATION: /note="synthetic construct"

<400> SEQUENCE: 4
ucacuccacc aucccaccc caccccaccc cacccc                      37

<210> SEQ ID NO 5
<211> LENGTH: 9
<212> TYPE: RNA
<213> ORGANISM: Artificial Sequence
<220> FEATURE:
<223> OTHER INFORMATION: /note="synthetic construct"

<400> SEQUENCE: 5 uuauuuauu                                                    9

<210> SEQ ID NO 6
<211> LENGTH: 10
<212> TYPE: DNA
<213> ORGANISM: Artificial Sequence
<220> FEATURE:
<223> OTHER INFORMATION: /note="synthetic construct"

<400> SEQUENCE: 6
ccaccccacc                                                  10

<210> SEQ ID NO 7
<211> LENGTH: 126

-continued

```
<212> TYPE: DNA
<213> ORGANISM: Artificial Sequence
<220> FEATURE:
<223> OTHER INFORMATION: /note="synthetic construct"

<400> SEQUENCE: 7
cgcgugagcg ugcgggaggg cuaggcccgu gcccccgccu gccaccggag gucacuccac      60 caucoccacc ccaccccacc ccaccccogc caugcaacgg gauugaaggg uccugccggu     120
gggacc                                                                126
```